US012734276B2

(12) United States Patent
Chen et al.

(10) Patent No.: US 12,734,276 B2
(45) Date of Patent: Sep. 15, 2026

(54) FLAT SELF-CURLING SHEET MEMBRANES AND METHODS FOR PRODUCING SAME

(71) Applicant: Collagen Matrix, Inc., Oakland, NJ (US)

(72) Inventors: Hui-Chen Chen, Wayne, NJ (US); Natsuyo Shishido Lee, Basking Ridge, NJ (US); Daniel Ammon, Webster, NY (US)

(73) Assignee: Collagen Matrix, Inc., Oakland, NJ (US)

( * ) Notice: Subject to any disclaimer, the term of this patent is extended or adjusted under 35 U.S.C. 154(b) by 285 days.

(21) Appl. No.: 18/290,109

(22) PCT Filed: May 5, 2022

(86) PCT No.: PCT/US2022/027933
§ 371 (c)(1),
(2) Date: Nov. 9, 2023

(87) PCT Pub. No.: WO2022/240657
PCT Pub. Date: Nov. 17, 2022

(65) Prior Publication Data

US 2024/0252724 A1 Aug. 1, 2024

Related U.S. Application Data

(60) Provisional application No. 63/187,705, filed on May 12, 2021.

(51) Int. Cl.
*A61L 27/46* (2006.01)
*A61L 27/54* (2006.01)

(52) U.S. Cl.
CPC .............. *A61L 27/46* (2013.01); *A61L 27/54* (2013.01); *A61L 2430/10* (2013.01);
(Continued)

(58) Field of Classification Search
None
See application file for complete search history.

(56) References Cited

U.S. PATENT DOCUMENTS 5,425,769 A * 6/1995 Snyders, Jr. ............ A61L 27/24 623/23.61
5,728,753 A 3/1998 Bonfield et al.
(Continued)

FOREIGN PATENT DOCUMENTS

WO 2001066044 A2 9/2001

OTHER PUBLICATIONS

Du.C., et al., Formation of calcium phosphate/collagen composites through mineralization of collagen matrix, J. Biomed. Mater. Res., 50 (Apr. 7, 2000) pp. 518-527. (Year: 2000).*
(Continued)

*Primary Examiner* — Dominic Lazaro
(74) *Attorney, Agent, or Firm* — Shumaker & Sieffert, P.A.

(57) ABSTRACT

A flat self-curling rollable composite sheet membrane, and methods for preparing such membranes. The sheet membrane includes a flat layer of collagen and a bioactive agent, such as a calcium phosphate-based mineral. The flat layer self-curls into a predetermined shape upon absorption of an aqueous fluid. The methods for preparing the membranes include the steps of adding mineral to a collagen dispersion, forming a composite collagen matrix having mineral particles dispersed therein, compressing the composite matrix between two plates to form a flat sheet, and drying the flat sheet to yield a rollable composite sheet membrane.

16 Claims, 2 Drawing Sheets

(52) U.S. Cl.
CPC ....... *A61L 2430/12* (2013.01); *A61L 2430/32* (2013.01); *A61L 2430/38* (2013.01)

(56) References Cited

U.S. PATENT DOCUMENTS

| | | | | |
|---|---|---|---|---|
| 5,977,204 | A | 11/1999 | Boyan et al. | |
| 6,090,996 | A | 7/2000 | Li et al. | |
| 6,391,333 | B1 | 5/2002 | Li et al. | |
| 9,061,464 | B2 * | 6/2015 | Li | A61F 2/04 |
| 9,308,219 | B2 | 4/2016 | Li et al. | |
| 2001/0037014 | A1 | 11/2001 | Liu | |
| 2010/0055149 | A1 | 3/2010 | Li et al. | |
| 2013/0004559 | A1 * | 1/2013 | Li | A61P 17/02 156/174 |

OTHER PUBLICATIONS

Gallinetti, S., et al., Development and Characterization of Biphasic Hydroxyapatite/β-TCP Cements, J. Am. Cer. Soc., 97 (2014) pp. 1065-1073. (Year: 2014).*

Extended Search Report from counterpart European Application No. 22808077.6 dated Mar. 10, 2025, 8 pp.

International Preliminary Report on Patentability from International Application No. PCT/US2022/027933 dated Nov. 14, 2023, 8 pp.

International Search Report and Written Opinion of International Application No. PCT/US2022/027933 dated Oct. 5, 2022, 11 pp.

Response to Extended Search Report dated Mar. 10, 2025, from counterpart European Application No. 22808077.6 filed Sep. 24, 2025, 14 pp.

Communication pursuant to Article 94(3) EPC from counterpart European Application No. 22808077.6 dated Mar. 11, 2026, 6 pp.

* cited by examiner

FLAT SELF-CURLING SHEET MEMBRANES AND METHODS FOR PRODUCING SAME

RELATED APPLICATION

This application claims priority to U.S. Provisional Patent Application No. 63/187,705, filed May 12, 2021, the disclosure of which is incorporated herein by reference in its entirety.

BACKGROUND OF THE INVENTION

Surgical procedures for repairing diseased or traumatic tissue wounds often require use of biocompatible and semi-permeable protective membranes to assist wound healing and tissue regeneration, so as to expedite recovery.

There is a need for membranes that better serve this purpose in medical and dental surgeries.

SUMMARY OF THE INVENTION

One aspect of this invention relates to a flat self-curling permeable sheet membrane. The definition of the "self-curling" is, upon hydration, the sheet membrane curls into itself (i.e., two edges of the sheet membrane converge towards each other), either with or without overlapping.

The membrane of this invention contains a matrix formed of crosslinked biopolymeric fibers, in which the matrix self-curls into a predetermined shape upon absorption of an aqueous fluid, is permeable to molecules having molecular weights not greater than $1\times10^6$ Daltons (e.g., $5.0\times10^5$ Daltons). In various embodiments, the membrane has a thickness of 0.2-1.2 mm (e.g., 0.4-0.8 mm), a density of 0.1-0.8 g/cm$^3$ (e.g., 0.4-0.7 g/cm$^3$), a hydrothermal shrinkage temperature of 50-85° C. (e.g., 52-80° C.), a suture pullout strength of 0.1-3.0 kg (e.g., 0.2-1.5 kg), an in vivo resorption time of 2-18 months (e.g., 3-12 months), a self-curling time of 10-80 seconds (e.g., 20-60 seconds), a tensile strength of 50-300 kg/cm$^2$ (e.g., 65-200 kg/cm$^2$), and a compression resistance of 0.1-10 N (e.g., 0.5-9 N).

Measurements of the thickness and density of the membrane described above are made in a dry state. On the other hand, measurements of the permeability, hydrothermal shrinkage temperature, suture pullout strength, in vivo resorption time, self-curling time, and tensile strength are made in a hydrated state (i.e., upon absorption of an aqueous fluid). As to the compression resistance, it can be measured either in a dry state or in a hydrated state. Actual examples of all these measurements are provided below.

The biopolymeric fibers used to prepare the membrane can be natural polymers, such as collagen, elastin, fibrin, and polysaccharides, genetically engineered materials, or a combination thereof. They can be oriented, i.e., at least half of the fibers in the sheet are in one general direction as determined by the method described in U.S. Pat. No. 6,391,333 or by an analogous method.

In various embodiments, the membrane of this invention contains a composite matrix formed of crosslinked biopolymeric fibers and a bioactive agent, which is included in the membrane of this invention to assist wound healing and tissue regeneration for functional recovery. Examples of bioactive agents include but are not limited to growth factors (e.g., platelet-derived growth factor, basic fibroblast growth factor, insulin-like growth factor, vascular endothelial growth factor, and nerve growth factor), cytokines (e.g., thrombopoietin and erythropoietin), glycosaminoglycans (e.g., hyaluronic acid, chondroitin sulfate), polysaccharides (e.g., chitosan, alginic acid, and cellulose), glycoproteins (e.g., mucins and luteinizing hormone), cell adhesive molecules (e.g., laminins and fibronectins), antibiotics (e.g., gentamycin, erythromycin, silver sulfadiazine, and tetracycline), anti-blood vessel stenosis agent (e.g., sinolimus and paclitaxel) and the like. The bioactive agent may be incorporated into the membrane via electrostatic interactions, physical or mechanical interactions, covalent bonding using crosslinking agents or light, a combination of the above, or via a spacer molecule that is well known in the art. Composite sheet membranes according to various embodiments of the invention are also formed of crosslinked biopolymeric fibers and minerals, as discussed below.

Another aspect of this invention relates to a method of preparing a flat self-curling rollable composite sheet membrane.

In one embodiment, the method includes the following steps: swelling a collagen dispersion in basic aqueous solution; homogenizing the collagen dispersion to obtain a uniform collagen dispersion; adding mineral particles to the collagen dispersion, wherein the weight ratio of collagen to mineral ranges from 3:97 to 60:40; blending the collagen dispersion and mineral particles to form a uniform mixture; transferring the collagen/mineral mixture into molds of a defined volume and geometry; freeze-drying the molded collagen/mineral mixture, whereby a composite collagen matrix having mineral particles dispersed therein is formed; rolling the freeze-dried composite matrix up to form a spiral implant with a desired amount of overlapping; inserting the composite matrix into a predetermined shape on a mold/mesh; crosslinking the composite matrix using a crosslinking agent to stabilize a shape of the composite sheet and to control its in vivo stability; subjecting the crosslinked composite matrix to series of water and/or buffer rinses to remove residual crosslinking agents therefrom; compressing the composite matrix between two plates to form a flat sheet; and drying the flat sheet to yield the rollable composite sheet membrane In another embodiment, the method includes the following steps: dispersing 10 g of collagen fibers and 10 g of mineral particles in 1,000 ml basic solution overnight; homogenizing the dispersion to form a uniform collagen/mineral mixture; adding additional mineral particles to the collagen/mineral mixture so that it has a final desired mineral content in the range of 40-97% by weight; de-airing the collagen/mineral mixture under vacuum; reconstituting the collagen/mineral mixture by adjusting the pH of the mixture to precipitate collagen fiber in forming a coacervate; dehydrating the coacervate collagen/mineral mixture to reduce the volume in producing a desired density composite; transferring the dehydrated collagen/mineral mixture into molds of a defined volume and geometry; freeze-drying the molded collagen/mineral mixture, whereby a composite collagen matrix having mineral particles dispersed therein is formed; rolling the freeze-dried composite matrix up to form a spiral implant with a desired amount of overlapping; inserting the rolled composite matrix into a cylindrical shaped mold/mesh; crosslinking the rolled composite matrix using a crosslinking agent to stabilize a shape of the composite sheet and to control its in vivo stability; subjecting the crosslinked composite matrix to series of water and/or buffer rinses to remove residual crosslinking agents therefrom; compressing the composite matrix between two plates to form a flat sheet; and drying the flat sheet to yield the rollable composite sheet membrane.

In another embodiment, the method includes the following steps: dispersing 3 g of collagen fibers in 200 ml acid solution overnight; homogenizing the dispersion to form a uniform dispersion; adding 27 g of mineral to the collagen dispersion; mixing the collagen dispersion and mineral; de-airing the collagen/mineral dispersion under vacuum; adjusting the pH of the dispersion to coacervate the collagen fibers; de-airing the resulting collagen/mineral mixture, partially dehydrating the collagen/mineral mixture by decanting the solution to reduce the volume to the desired product density; pouring the dehydrated collagen/mineral mixture into a stainless steel tray; freeze-drying the dehydrated collagen/mineral mixture, whereby a composite collagen matrix having mineral particles dispersed therein is formed; rolling the freeze-dried composite matrix up to form a spiral implant with a desired amount of overlapping; inserting the rolled composite matrix into a cylindrical shaped mold/mesh; crosslinking the rolled composite matrix using a crosslinking agent to stabilize a shape of the composite sheet and to control its in vivo stability; subjecting the crosslinked composite matrix to series of water and/or buffer rinses to remove residual crosslinking agents therefrom; compressing the composite matrix between two plates to form a flat sheet; and drying the flat sheet to yield the rollable composite sheet membrane.

Also within the scope of this invention are flat self-curling permeable sheet membranes prepared by the above-described method.

One embodiment of the invention includes a flat self-curling composite sheet membrane comprising a flat layer of collagen and a bioactive agent, wherein the flat layer self-curls into a predetermined shape upon absorption of an aqueous fluid.

Another embodiment of the invention includes a flat self-curling composite sheet membrane consisting of a flat layer of collagen and a bioactive agent, wherein the flat layer self-curls into a predetermined shape upon absorption of an aqueous fluid.

The membrane of this invention, due to its flat shape, has an advantage of being easily stored and transported.

The details of one or more examples of the invention are set forth in the description below. Other features, objects, and advantages of the invention will be apparent from the detailed description of the examples and also from the drawing and the appending claims.

BRIEF DESCRIPTION OF THE DRAWINGS

Embodiments of the invention are further described but are in no way limited by the following illustrations.

DETAILED DESCRIPTION OF THE INVENTION

Figure 1:
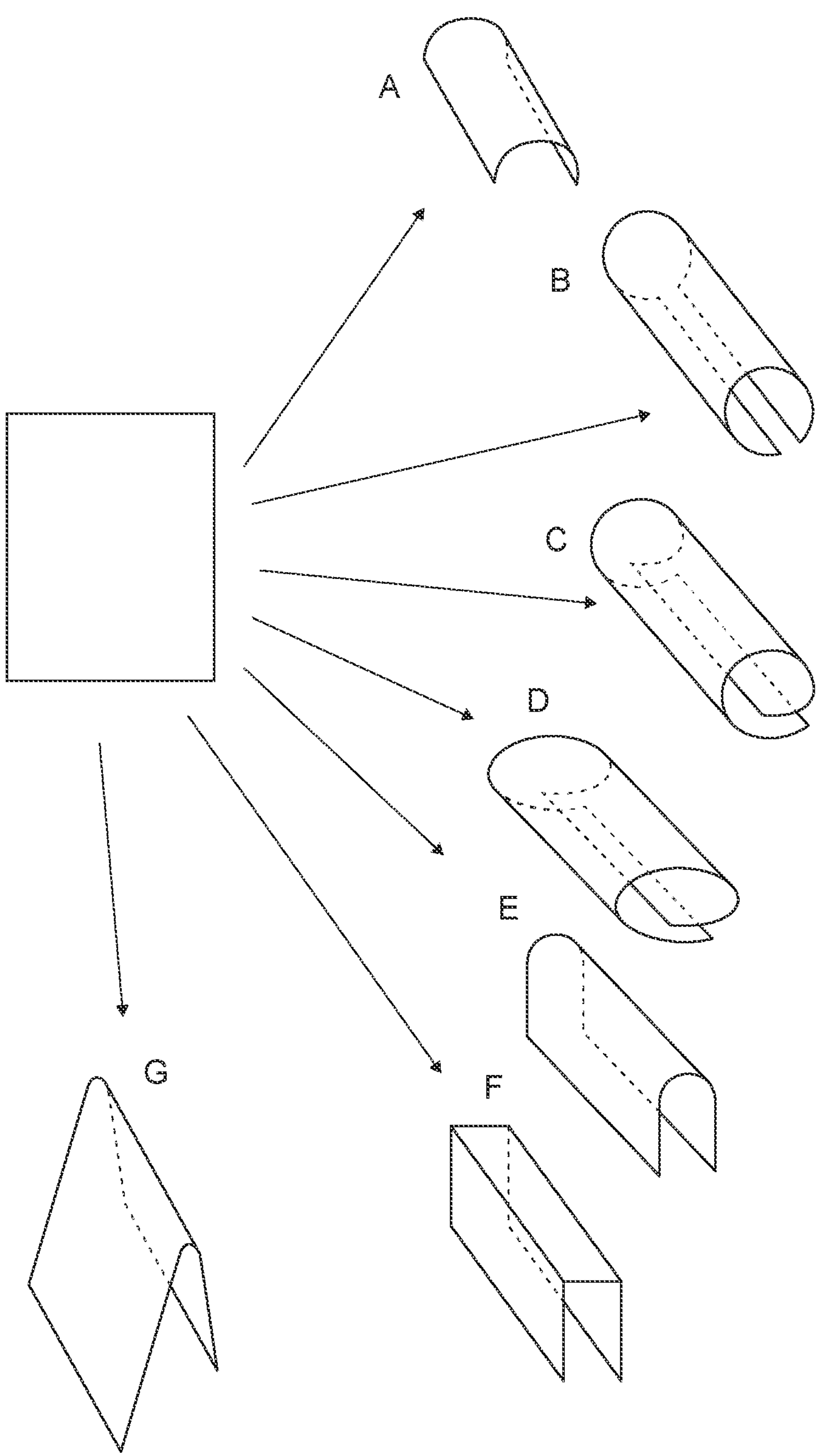
FIG. 1 is a schematic diagram that illustrates folding a flat sheet membrane according to embodiments of the present invention into seven different shapes.

This invention is based on an unexpected discovery that a flat permeable sheet membrane can self-curl into a predetermined shape upon absorption of an aqueous fluid. It is permeable to molecules having molecular weights not greater than $1\times10^6$ Daltons.

Such a flat self-curling permeable sheet membrane can be used as a resorbable and implantable device for better assisting wound healing and tissue regeneration. More specifically, the flat permeable sheet membrane is facile for insertion and placement around a surgical wound site, as upon absorption of an aqueous fluid, it self-curls into a pre-determined shape which conforms to an injury site.

In various embodiments, the membranes of the present invention are composites of a biopolymeric material, such as collagen, and minerals, as further discussed below. In other embodiments, the membranes are formed from a biopolymeric material only.

Type I collagen fibers are the preferred biopolymeric material for preparing the membranes of the present invention due to their biocompatibility and ease in accessing large quantities of the material from animal source. Other biopolymeric materials, which can be natural or synthetic, include but are not limited to, other types of collagen (e.g., type II to type XXI), elastin, fibrin, polysaccharide (e.g., chitosan, alginic acid, cellulose, and glycosaminoglycan), a synthetic analog of a biopolymer by genetic engineering techniques, or a combination thereof.

Provided below are exemplary procedures for fabricating type I collagen-based membranes of this invention. Such procedures are also disclosed in U.S. Pat. No. 9,308,219.

An acid dispersion of type I collagen fibers with a solid content of about 0.5 to 1.0% (w/w) is first prepared. Both inorganic and organic acids can be used. However, organic acids are preferred (e.g., lactic acid). Typically, a 0.05 M to 0.1 M lactic acid dispersion of collagen has a pH about 2.3 to 2.5. The dispersed collagen fibers are homogenized using a commercial homogenizer to mechanically disintegrate the fibers into smaller fibrils. After removal of air bubbles by vacuum, the dispersed fibrils are reconstituted into long fibers by adjusting the pH to about 4.7, the isoelectric point of the purified collagen as prepared by methods described in U.S. Pat. Nos. 6,391,333 and 9,061,464.

The reconstituted collagen fibers are then preferentially oriented circumferentially onto a rotating mandrel having a defined outer diameter with a rotational speed preferably greater than 40 RPM, and dried (e.g., freeze-dried) by methods well known in the art. The dried tubular membrane is then removed from the mandrel by cutting open along the longitudinal direction (parallel to the axis of the mandrel) using a scalpel to form a permeable sheet membrane. U.S. Pat. No. 6,391,333 discloses the above-described method for preparing a permeable sheet membrane made of oriented biopolymeric fibers. A dried permeable membrane can also be formed from the reconstituted biopolymeric fibers without orientation by the method described in U.S. Pat. No. 6,090,996.

Subsequently, the sheet membrane is hydrated (e.g., humidified in a humidification chamber) so that it can be easily folded into different shapes. The sheet membrane in a hydrated state is mechanically folded into a predetermined shape as shown in FIG. 1. If the membrane is made of oriented biopolymeric fibers, it is preferred that the shape follow, to the extent possible, the configuration of the pre-cut tubular membrane, which is circumferentially inward. The folded membrane is inserted into or wrapped around and fixed to a rigid metal/plastic mesh of a similar size and shape, before it is crosslinked using a crosslinking agent such as an aldehyde (e.g., formaldehyde vapor) to fix and preserve the predetermined shape. Other crosslinking agents with sufficient vapor pressure can also be used. Unreacted crosslinking agent can be removed by rinsing with water. The crosslinked membrane is hydrated (e.g., humidifying or its equivalent) to facilitate its flattening. As an example, the hydrated membrane can be converted into a flat sheet by compressing it within two plates. Finally, the flat membrane is dried before use. The thus-obtained flat membrane self-curls into the predetermined shape upon absorption of an aqueous liquid.

If a membrane is made of biopolymeric fibers without orientation, the permeable membrane, prepared from reconstituted fibers in an aqueous dispersion, needs not be fully dried so that it can be directly folded into a predetermined shape in a hydrated state. The membrane can be fully dried after it has been folded, if necessary or desired, before crosslinking the fibers.

The extent of crosslinking determines the in vivo stability of the membrane. Depending on the functional requirements in vivo, the extent of crosslinking may be controlled accordingly. More specifically, the extent of crosslinking in solution phase may be controlled by a crosslinking agent, concentration, temperature, pH, and time of crosslinking. The crosslinking in vapor may be controlled by vapor pressure, temperature, and time of crosslinking. In vivo stability depends on the nature of the crosslinks formed by various crosslinking agents. Generally, glutaraldehyde forms more stable crosslinks than formaldehyde and carbodiimide. Thus, glutaraldehyde has been used to crosslink tissue heart valves for in vivo durability, and formaldehyde has often been used to crosslink resorbable implants.

The extent of crosslinking may be determined by methods well known in the art such as by monitoring the hydrothermal shrinkage temperature. In other words, the hydrothermal shrinkage temperature of a crosslinked membrane is correlated to the in vivo resorption time. For example, using formaldehyde vapor as a crosslinking agent, as described in Yuen et al., Trans Six World Biomaterials Congress, page 222 (2000), the hydrothermal shrinkage temperature of the as-formed membrane is in the range from about 48° C. to about 70° C. corresponding to an in vivo resorption time in the range of 2 to 12 months.

The membranes of this invention can be used to in different surgical procedures, e.g., tendon/ligament repair, peripheral nerve repair, vascular repair, dental surgery, and orthopedic/spine surgery.

Without further elaboration, it is believed that one skilled in the art can, based on the disclosure herein, utilize the present invention to its fullest extent. The following specific examples are, therefore, to be construed as merely descriptive, and not limitative of the remainder of the disclosure in any way whatsoever. All publications and patents cited herein are incorporated by reference.

Preparation of Collagen Fibers

Bovine flexor tendon was cleaned by removing fat and fascia, and washing with water. The cleaned tendon was frozen and comminuted into 0.5 mm slices with a meat slicer. One kilogram of the sliced wet tendon was subsequently extracted with 5 L of distilled water and with 5 L of 0.2 N HCl/0.5 M $Na_2SO_4$ at room temperature for 24 hours, the extracts were discarded. The residual acid on the tendon was removed by washing with 5 L of 0.5M $Na_2SO_4$ solution. The tendon was again extracted with 5 L of 0.75 M NaOH/1.0 M $Na_2SO_4$ solution at room temperature for 24 hours. The extract was also discarded. The residual base was neutralized with a 0.01N HCl solution to pH 5, followed by several washes with distilled water to remove the residual salts on the purified tendon. The tendon was then defatted at 25° C. under constant agitation with isopropanol of 5 times the volume of the tendon for 8 hours and an equal volume of the tendon overnight. The defatted tendon was then air-dried and stored at room temperature until further processing.

Preparation of a Collagen Fiber Dispersion

An aliquot of the insoluble collagen fibers was weighed and dispersed in 0.07 M lactic acid, homogenized with a Silverson Homogenizer (East Longmeadow, Mass.), and filtered with a 30 mesh stainless steel mesh filter to obtain a dispersion containing 0.7% (w/v) collagen. The dispersion was de-aerated under vacuum to remove the air trapped in the dispersion and stored at 4° C. until use.

Preparation of Flat Self-Curling Permeable Sheet Membranes

An aliquot of the acid dispersed collagen fibers prepared above was reconstituted by adding 0.6% $NH_4OH$ to adjust the pH of the dispersion to the isoelectric point of collagen (pH 4.5-5.0). The reconstituted fibers were poured into a fabrication device which was set up with the insertion of a mandrel of 1.9 cm in diameter. The fibers were evenly distributed along the mandrel while the mandrel was rotated at a speed of 40-50 rpm. The excess solution was removed by compressing the hydrated fibers on the rotating mandrel against two plates that precisely control the thickness of the wall of the membrane.

The partially dehydrated collagen fibers were freeze-dried at −10° C. for 24 hours and at 20° C. for 16 hours under a pressure less than 200 millitorr using a Virtis Freeze Dryer (Gardiner, N.Y.). The freeze-dried tubular matrix was removed from the mandrel and cut along the longitudinal direction. The tubular sheet membrane was then humidified in an environment of 80-100% humidity for 1-8 hours. The humidified membrane was mechanically formed onto the mold of defined size and shape as that shown in FIG. 1. The formed membrane was chemically crosslinked with formaldehyde vapor at the humidity of 90-95% for 3-6 hours to stabilize the shape and to control its in vivo stability. The crosslinked matrix was rinsed in water to remove the residual formaldehyde and freeze-dried. The shaped membrane was then humidified again and mechanically formed into a flat sheet between two mesh plates. The flat sheet was then air dried.

Characterization of Flat Self-Curling Permeable Sheet Membranes

Physicochemical and mechanical characteristics of flat self-curling membranes were assessed in the following aspects:

i) Thickness

The thickness of a sample was first measured on all four sides with a caliper (Mitutoyo, Japan). The average value of four measurements represents the thickness of the membrane.

ii) Density

A sample was dried under $P_2O_5$ for 24 hours and the dry weight recorded. The dimensions of the sample were measured with a caliper (Mitutoyo, Japan) to calculate the volume. The density was determined as the weight of the product per unit volume.

iii) Tensile Strength

A sample was cut into a dumbbell shape with a die punch and soaked in purified water for 3-5 minutes. The sample was then secured to a clamp fixture of a mechanical tester (Chatillon, Greenboro, N.C.), and pulled at a speed of 2.54 cm/min until the sample pulled apart. The tensile strength in the unit of $kg/cm^2$ was recorded.

iv) Hydrothermal Shrinkage Temperature

The hydrothermal shrinkage temperature ($T_s$) was determined by a measurement of the thermal transition temperature of the hydrated collagen matrix. A circular sample was punched, hydrated in phosphate buffer, pH 7.4, sealed in an aluminum cell, placed in a differential scanning calorimeter (Mettler-Toledo, Inc. Columbus, Ohio) and heated at a rate of 5° C./min. The $T_s$ was taken as the onset temperature of the transition from the triple helical structure to a denatured structure.

v) Self-Curling Time

A sample in its dry flat state was placed in a beaker with purified water. The timer was started as soon as the sample was placed into the water. The timer was stopped when the sample had returned to its original pre-determined shape.

vi) Compression Resistance

A sample was placed onto a metal plate with the open-ended sides facing down. The compression plate was then slowly brought down onto the sample. The sample was considered to be compressed when no light was visible through the sample and the plate. This test can be performed hydrated or dry, with the sides fixed or unfixed.

vii) In Vivo Stability

The in vivo stability and resorbability of a tissue wrap implant membrane was determined by the following experiment: Collagen membrane materials with different hydrothermal shrinkage temperatures were implanted subcutaneously in rats. At predetermined time points the rats were sacrificed and the amount of residual collagen implants remaining was determined by histological means. The total resorption time of each membrane material was obtained by extrapolation of the residual amount of collagen as a function of time to a value where the area occupied by the residual implant collagen was less than 2%. The total resorption time and the hydrothermal shrinkage temperature of the membranes has a linear relationship (Yuen, et al., Trans Soc. Biomaterials, 2000).

Based on the relationship, a membrane matrix material can be selected for certain in vivo stability, based on its hydrothermal shrinkage temperature. For example, if the desired in vivo stability is 4-6 months, a hydrothermal shrinkage temperature of a flat self-curling membrane in the range 50-55° C. will be suitable.

viii) Suture Pullout Strength

Suture pullout strength was determined as follows: A membrane was cut to a size of 20 mm×15 mm and soaked in pH 7.4 phosphate buffered saline (PBS) at 25° C. for about 5 minutes. A suture (3-0 silk black braided, taper SH-1, Ethicon, Somerville, N.J.) was placed through the 20 mm membrane side at approximately 3 mm from the edge. The suture was tied into a knot, secured to the hook adapter of the tensile tester, clamped, and pulled at a speed of 2.54 cm/minute until the suture was pulled out and pull-out strength recorded.

ix) Permeability

A 2-cm diameter disk cut from a membrane of this invention was inserted into a two compartment chamber containing PBS. A fixed volume of PBS containing 50 μg of various sizes of peptide and protein molecules per mL was added to one compartment. The solution in both compartments was allowed to equilibrate for 24 hours. A colorimetric assay was then conducted to determine the amount of peptide or protein molecules in the compartment which initially only contained PBS.

The results of the characterization studies are summarized in Table 1 below:

TABLE 1

| Property | Value |
|---|---|
| Thickness (mm) | 0.53 ± 0.03 |
| Density (g/cm$^2$) | 0.61 ± 0.04 |
| Tensile Strength (kg/cm$^2$) | 97.3 ± 1.9 |
| Hydrothermal Shrinkage Temperature (° C.) | 71.5 ± 0.4 |
| Self-curling Time (sec) | 46.7 ± 1.5 |
| Compressive Resistance (N) (the sides of the samples were not fixed) | 0.96 ± 0.02 (hydrated)<br>5.1 ± 0.03 (dry) |
| Compressive Resistance (N) (the sides of the samples were fixed to a rigid block) | 2.07 ± 0.16 (hydrated)<br>7.62 ± 0.45 (dry) |

*All samples were sterilized via gamma sterilization

Use of a Flat Self-Curling Permeable Sheet Membrane in Tendon/Ligament Repair

Local, regional or general anesthesia is administered to the patient depending on the extent and location of tendon damage. After the overlying skin has been cleaned with an antiseptic solution and covered with a sterile drape, a surgeon makes an incision over the injured tendon. When the tendon has been located and identified, the surgeon sutures the damaged or torn ends of the tendon together. If the tendon is severely injured, a tendon autograft may be required. This is a procedure in which a piece of tendon is taken from the foot or other part of the body and used to repair the damaged tendon. After the tendon is repaired, a membrane sheet of the present invention is placed above or under the repaired tendon. If the injured site has sufficient body fluid to hydrate the membrane, the membrane sheet self-curls (FIGS. 1, C and D) to form a wrap around the injured tendon to protect the wound site and assist the wound healing of the tendon. A small amount of sterile saline may be added to the membrane to accelerate the self-curling of the membrane.

Use of a Flat Self-Curling Permeable Sheet Membrane in Peripheral Nerve Repair

Local, regional or general anesthesia is administered to a patient depending on the extent and location of nerve damages. After the overlying skin has been cleaned with an antiseptic solution and covered with a sterile drape, a surgeon makes an incision to locate and identify the injured nerve. If the nerve injury is fresh and the nerve is severed, the surgeon performs a suture repair procedure to reconnect the proximal and distal stumps of the nerve. After repair, a sheet membrane described in the invention is placed over or under the repair site. If the injured site has sufficient body fluid to hydrate the membrane, the membrane sheet self-curls to form a wrap (FIGS. 1, C and D) around the injured nerve to protect the wound site, minimize the axon escaping from the suture line and assist the wound healing of the nerve. If the nerve is severely injured and a piece of the nerve is lost, the surgeon transplants an autograft, such as a sural nerve from the back of the lower leg, to the injured site to bridge the nerve gap and a membrane of the present invention is used similarly as described above.

Use of a Flat Self-Curling Permeable Sheet Membrane in Vascular Repair

Bypass surgery is an open procedure that requires general anesthesia. In femoropopliteal or femorotibial bypass, after a patient is prepared for the procedure, a surgeon makes an incision in the groin and thigh to expose the affected artery above the blockage, and another incision (e.g., behind the knee for the popliteal artery) to expose the artery below the blockage. The arteries are blocked off with vascular clamps. If an autologous graft is used, the surgeon passes a dissected (cut and removed) segment of the saphenous vein along the artery that is being bypassed. If the saphenous vein is not long enough or is not of good quality, a vascular graft of synthetic material is used. The surgeon sutures the graft into an opening in the side of one artery and then into the side of the other. Plain sheet membranes of the present invention are placed at the anastomotic sites, self-curled (FIGS. 1, B and C) to conform at the anastomotic sites to serve their intended functions. In a femoropopliteal bypass surgery, for example, the graft extends from the femoral artery to the popliteal artery. The clamps are then removed and the flow of blood is observed to make sure it bypasses the blocked portion of the affected artery.

Use of a Flat Self-Curling Permeable Sheet Membrane in Dental Surgery

Ridge augmentation: A cut is made along the center of the gum tissue to expose the underlying bone. A selected bone grafting material is placed above the bone such that the overall height of the bone with the bone graft is sufficient to maintain the stability of the dental tooth root (a titanium screw). At this stage, a membrane of the present invention is placed over the bone graft material and hydrated with saline if needed so that the membrane self-curls to the predetermined shape and size (FIGS. 1, E and G). The gum tissue is then sutured over the membrane. The new bone growth and maturation generally takes about 4-8 months.

Dental implantation: A dental implant restoration is commonly composed of a titanium material screw and a crown. A small-diameter hole (pilot hole) is drilled at edentulous jaw sites (after the ridge height is restored) in order to guide the titanium screw that holds a dental implant in place. After the initial pilot hole has been drilled into the appropriate jaw site, it is slowly widened to allow placement of the implant screw. Once in place, surrounding gum tissue is secured over the implant and a protective cover screw is placed on top to allow the site to heal and osseo-integration to occur. After up to six months of healing, the clinician uncovers the implant and attaches an abutment (which holds the crown or tooth-like replacement) to the implant. When the abutment is in place, the clinician creates a temporary crown. The temporary crown serves as a template around which the gum grows and shapes itself in a natural way. The process is completed when the temporary crown is replaced with a permanent crown.

Use of a Flat Self-Curling Permeable Sheet Membrane in Orthopedic/Spine Surgery

Patients are given a general anesthesia to put them to sleep during most spine surgeries. During surgery, the patient's knees face down on an operating table. An incision is made down the middle of the low back. The tissues just under the skin are separated. Then the small muscles along the sides of the low back are lifted off the vertebrae, exposing the back of the spinal column. Next, a surgeon takes an X-ray to make sure that the procedure is being performed on the correct vertebrae.

The surgeon first removes any pressure from nearby nerves. This may involve removing part or all of the lamina bone. Then the surgeon takes out any disc fragments and scrapes off nearby bone spurs. In this way, the nerves inside the spinal canal are relieved of additional tension and pressure. To prepare the area to be fused, the surgeon shaves a layer of bone off the back surfaces of the spinal column. The cut bone bleeds. The surgeon lays the biological bone graft (pre-saturated with bone marrow aspirate) over the back of the spinal column. A membrane of the present invention is then laid over the bone graft material and membrane self-curls (FIGS. 1, A and F) upon hydration with body fluid (e.g., blood) or hydrated with small amount of sterile saline to contain the bone graft material and prevent fibrogenic cells entering the grafted space. The body heals (or fuses) the bones together when bone graft is in contact with the bleeding bone area.

During posterior spinal fusion, the surgeon also fixes the bones in place using a combination of metal screws, rods, and plates. This instrumentation (or hardware, as it is sometimes called) holds the vertebrae to be fused together and prevents them from moving. The less motion there is between two bones trying to heal, the higher the chance they will successfully fuse. The use of instrumentation has increased the success rate of spinal fusions considerably. A drainage tube may be placed in the wound. The muscles and soft tissues are put back in place, and the skin is stitched together.

Composite Sheet Membrane

In various embodiments, the sheet membrane disclosed herein is a composite that includes collagen fibers or another biopolymeric material (as described above) and one or more bioactive agents (as also discussed above), such as minerals. Examples of such minerals include but are not limited to β-TCP (tricalcium phosphate), BiPhasic (Hydroxyapatite/β-TCP), Calcium Sulfate and Hydroxyapatite from natural sources or synthetic derived where applicable. BioGlass can be added as a mineral as well. An example of calcium phosphate-based minerals/ceramics is discussed in Example 1 below.

Unless otherwise indicated below, the composite sheet membranes are formed using the same or similar methods as described above in connection with the sheet membranes formed from only collagen fibers or other biopolymeric materials. The composite sheet membranes described herein also have the same surgical and therapeutic applications as discussed above in connection with the sheet membranes formed from only collagen fibers or other biopolymeric materials.

In various embodiments, the composite sheet membrane has the following distributions (in weight percentage) of collagen fibers and mineral:

5% collagen fibers and 95% mineral;
10% collagen fibers and 90% mineral;
15% collagen fibers and 85% mineral;
20% collagen fibers and 80% mineral;
25% collagen fibers and 75% mineral; and
30% collagen fibers and 70% mineral.

The composite sheet membranes having these distributions constitute an invention that is based on an unexpected discovery, given that their respective collagen fiber content is relatively low (i.e., 5%-30%), yet the composite sheets still exhibit behavior indicative of a higher collagen fiber content (i.e., by self-curling into a pre-determined shape upon absorption of an aqueous fluid).

The following specific examples of methods for producing the composite sheet membrane are to be construed as merely descriptive, and not limitative of the remainder of the disclosure in any way whatsoever.

Example 1

A collagen dispersion (0.6-1.5% by weight) is swollen in basic aqueous solution and homogenized using a homogenizer to obtain a uniform collagen dispersion. In one embodiment, a Silverson homogenizer (East Longmeadow, Mass.) is used. Other brands/types of homogenizers, mixers or blenders can be used in other embodiments.

Calcium phosphate-based minerals and/or ceramics are then added to the collagen dispersion. In various embodiments, the calcium phosphate-based minerals and/or ceramics can be formed of calcium sulfate or calcium phosphate compounds of various compositions. Examples of calcium phosphate compounds include tricalcium phosphate, tetra calcium phosphate, and hydroxyapatite. The particles can also be an organic bone mineral, carbonate apatite or a mixture of this compound with any of the above-mentioned calcium-containing compounds. More detail about calcium- and silicate-based minerals and ceramics can be found in LeGeros, Raquel Z., Calcium Phosphate Materials in Restorative Dentistry: A Review. *Adv. Dent. Res.,* 1988, 2(1): 164-180; U.S. Pat. Nos. 5,977,204, and 5,728,753.

Alternatively, calcium-containing silicate-based glasses such as 45S5 bioglass can be incorporated into the composite matrix. Examples of preferred bioactive glasses suitable comprising calcium-phosphorous-sodium-silicate or calcium-phosphorous-silicate, also include 45S5 glass, glass ceramic 58S5, S53P4, 13-93.

The ratio of weight percent of collagen to mineral is predetermined to define the final composition of the composite. The weight ratio of the collagen fibers and mineral ranges from 3:97 to 60:40, with a preferred collagen to mineral weight ratio in the range of 30:70 to 10:90 (i.e., mineral content of 70-90% by weight). The collagen dispersion and mineral particles are then gently blended to form a uniform mixture.

The above collagen/mineral mixture is then transferred into molds of a defined volume and geometry. In various embodiments, the mold volume ranges from 5 cc-40 cc. In some embodiments, the composite mixture is formed by a mold into square or rectangular shapes with various heights (i.e., cuboid or rectangular cuboid), depending upon the desired volume. For example, the mixture is transferred into a mold having a rectangular cuboid shape (i.e., 10 cm in length×6 cm in width×2-3 mm height).

The molding step is followed by a freeze-drying step using a freeze dryer. Upon completion of freeze drying, a collagen mineral mixture having a porous collagen matrix and mineral particles dispersed therein is formed.

Example 2

10 g of collagen fibers and 10 g of mineral particles are dispersed in 1,000 ml basic solution overnight. The dispersion is homogenized with a Silverson homogenizer or blender to form a uniform mixture. Additional mineral particles are then added to the final desired mineral content (40-97%) and de-aired under vacuum.

The above collagen mineral mixture is then reconstituted by adjusting the pH of the mixture to precipitate collagen fiber in forming a coacervate. The resulting coacervate is then dehydrated to reduce the volume in producing desired density composite and transferred into molds of a defined volume and geometry followed by a freeze-drying step using a freeze dryer. Upon completion of freeze drying, a collagen mineral mixture having a porous collagen matrix and mineral particles dispersed therein is formed.

Example 3

3 g of collagen fibers is dispersed in 200 ml acid solution overnight. The dispersion is then homogenized with a Silverson homogenizer or blender to form a uniform dispersion. To the collagen dispersion, 27 g of mineral is then added. The mixture is mixed using a blender for 1 minute and de-aired under vacuum. The pH of the dispersion was adjusted to coacervate the collagen fibers. The resultant mixture was de-aired under vacuum, partially dehydrated by decanting the solution to reduce the volume to the desired density of product, poured into a stainless steel tray and freeze dried.

Figure 2:
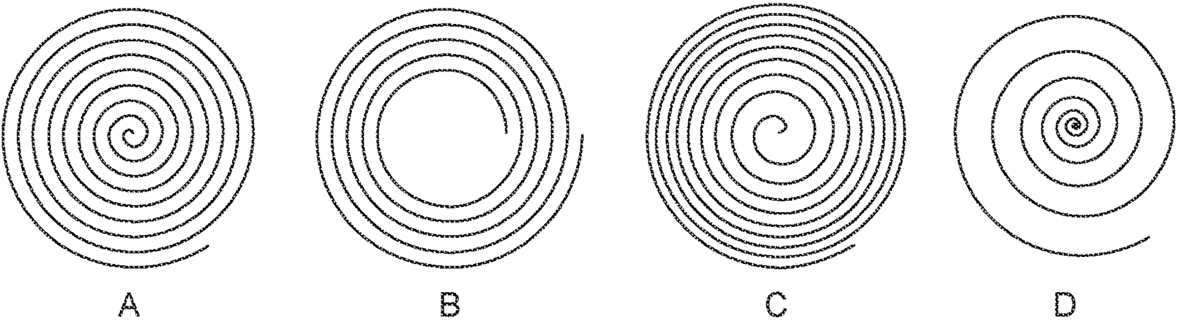
FIG. 2 is a schematic diagram of different rolled configurations of the flat self-curling sheet membrane according to embodiments of the present invention.

The final freeze-dried composite matrix/sheet prepared from Examples 1-3 above is then rolled up to form a spiral implant with a desired amount of overlapping. Various rolled configurations of the spiral implant with different amounts of overlapping are shown in FIG. 2 The desired amount of overlapping is based on the diameter of the tube (i.e., mandrel) used to rolled up the sheet in forming a spiral implant. The smaller diameter of the tubes used; the higher the amount of overlapping is created in the spiral implant. As shown in FIG. 2, the diameter of the tubes increases in order of B>C>A>D. However, the amount of overlapping also depends on the dimension of the freeze-dried sheet. Giving the same diameter of the tube used, a longer sheet will produce more overlapping than a shorter sheet.

Also relevant is the clinical application or significance of the desired amount of overlapping. Some applications might not require overlap as long as the implant can be shaped in different configuration as seen in the attached picture. For example, only configurations shown in FIGS. 1, C and D include overlapping (and not configurations A, B, E, F, G in FIG. 1). The definition of the "self-curling" is, upon hydration, that the sheet membrane curls into itself (i.e., two edges of the sheet membrane converge towards each other), either with or without overlapping.

The rolled composite is inserted into a cylindrical shaped mold/mesh, and then crosslinked using a crosslinking agent such as an aldehyde to stabilize the shape and to control its in vivo stability. The crosslinked composite matrix is then subjected to series of water and/or buffer rinses to remove residual crosslinking agents. The final rinsed composite sheet is then mechanically formed into a flat sheet between two plates. The flat sheet is then air dried or freeze dried to yield final rollable composite sheet.

The extent of self-curling by the composite sheet membrane is at least in part controlled by shaping the freeze-dried matrices into various pre-determined shapes such as a tube, an arch, or a channel as shown in FIG. 1. The extend of self-curling by the composite sheet membrane is also controlled at least in part by the extent of crosslinking.

Suitable collagens for inclusion in the composite matrix/sheet can include, in various embodiments, collagen that comprises up to 100% Type I collagen or up to about 90% of Type I collagen with up to about 5% of Type III collagen or up to about 5% of other types of collagen. Type I collagens include native fibrous insoluble human, bovine, porcine, or synthetic collagen, soluble collagen, reconstituted collagen, or combinations thereof. The insoluble collagen includes but not limited to collagen fibrils and fibers from tendon, ligament, skin, or bone of mammals. For example, it can be derived from the corium, which is the collagen-rich layer of an animal hide that is situated between the epidermis and the subcutaneous fat.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other examples are also within the claims.

In general, any combination of disclosed features, components and methods described herein is possible. Steps of a method can be performed in any order that is physically possible.

All cited patents, patent publications and non-patent references are incorporated by reference herein in their entireties.

Although embodiments have been disclosed, the invention is not limited thereby.

The invention claimed is:

1. A flat self-curling composite sheet membrane comprising a flat layer of collagen and a bioactive agent, wherein the flat layer is configured to self-curl into a predetermined shape upon absorption of an aqueous fluid, and wherein the bioactive agent comprises at least one mineral, the at least one mineral comprising at least one of calcium sulfate, a bioactive glass, or a calcium phosphate compound, and wherein the ratio of the collagen to the bioactive agent is within a range of 30:70 to 5:95.

2. The sheet membrane of claim 1, wherein the calcium phosphate compound is selected from a group consisting of tricalcium phosphate, tetra calcium phosphate, and hydroxyapatite.

3. The sheet membrane of claim 1, wherein the at least one mineral is natural or is synthetically derived.

4. The sheet membrane of claim 1, wherein the at least one mineral is selected from a group consisting of (i) anorganic bone material, (ii) natural carbonate apatite, and (iii) a mixture consisting of carbonate apatite and one or more calcium-containing compounds.

5. The sheet membrane of claim 1, wherein the at least one mineral is selected from a group consisting of synthetically derived β-TCP (tricalcium phosphate), hydroxyapatite, biphasic mineral, and calcium containing compounds.

6. The sheet membrane of claim 5, wherein the biphasic mineral is hydroxyapatite/β-TCP.

7. The sheet membrane of claim 1, wherein the collagen is selected from a group consisting of Type I collagen, Type III collagen, and a mixture of Type I and Type III collagen.

8. The sheet membrane of claim 1, wherein the predetermined shape is selected from a group consisting of a V, a tube, an arch, and a channel.

9. A flat self-curling composite sheet membrane consisting of a flat layer of collagen and a bioactive agent, wherein the flat layer is configured to self-curl into a predetermined shape upon absorption of an aqueous fluid, and wherein the bioactive agent consists of at least one mineral, the at least one mineral consisting of at least one of calcium sulfate, a bioactive glass, or a calcium phosphate compound, and wherein the ratio of the collagen to the bioactive agent is within a range of 30:70 to 5:95.

10. The sheet membrane of claim 9, wherein the predetermined shape is selected from a group consisting of a V, a tube, an arch, and a channel.

11. The sheet membrane of claim 9, wherein the calcium phosphate compound is selected from a group consisting of tricalcium phosphate, tetra calcium phosphate, and hydroxyapatite.

12. The sheet membrane of claim 9, wherein the at least one mineral is natural or is synthetically derived.

13. The sheet membrane of claim 9, wherein the at least one mineral is selected from a group consisting of (i) anorganic bone material, (ii) natural carbonate apatite, and (iii) a mixture consisting of carbonate apatite and one or more calcium-containing compounds.

14. The sheet membrane of claim 12, wherein the at least one mineral is selected from a group consisting of synthetically derived β-TCP (tricalcium phosphate), hydroxyapatite, biphasic mineral, and calcium containing compounds.

15. The sheet membrane of claim 14, wherein the biphasic mineral is Hydroxyapatite/β-TCP.

16. The sheet membrane of claim 9, wherein the collagen is selected from a group consisting of Type I collagen, Type III collagen, and a mixture of Type I and Type III collagen.

* * * * *